(12) United States Patent
Wallace et al.

(10) Patent No.: US 9,211,374 B2
(45) Date of Patent: Dec. 15, 2015

(54) THERAPEUTIC IMPLANTABLE DEVICE

(76) Inventors: Robert F. Wallace, Fort Myers, FL (US); Matthew Q. Shaw, Carmel, IN (US)

( * ) Notice: Subject to any disclaimer, the term of this patent is extended or adjusted under 35 U.S.C. 154(b) by 564 days.

(21) Appl. No.: 13/481,426

(22) Filed: May 25, 2012

(65) Prior Publication Data

US 2013/0317424 A1    Nov. 28, 2013

(51) Int. Cl.
*A61M 5/00*     (2006.01)
*A61M 31/00*    (2006.01)
*A61L 31/16*    (2006.01)
*A61L 31/14*    (2006.01)
*A61F 2/92*     (2013.01)

(52) U.S. Cl.
CPC .............. *A61M 5/00* (2013.01); *A61L 31/148* (2013.01); *A61L 31/16* (2013.01); *A61M 31/002* (2013.01); *A61F 2/92* (2013.01); *A61L 2300/61* (2013.01)

(58) Field of Classification Search
CPC ..... A61M 31/00; A61M 31/002; A61M 1/12; A61M 2205/04; A61M 5/00; A61F 2002/072; A61F 2210/0704; A61F 2250/0067; A61F 2/92; A61F 2/93; A61L 31/148; A61L 31/16; A61L 2300/61; A61K 9/0024; A61K 47/34
See application file for complete search history.

(56) References Cited

U.S. PATENT DOCUMENTS

| | | | |
|---|---|---|---|
| 5,580,569 A | 12/1996 | Giampapa | |
| 5,989,579 A | 11/1999 | Darougar et al. | |
| 6,090,996 A * | 7/2000 | Li | A61L 31/044 606/151 |
| 6,117,168 A * | 9/2000 | Yang | A61F 2/82 623/1.44 |
| 6,251,090 B1 | 6/2001 | Avery et al. | |
| 6,260,699 B1 * | 7/2001 | Kaplan | A01N 37/36 206/339 |
| 6,589,225 B2 | 7/2003 | Orth et al. | |
| 7,582,080 B2 | 9/2009 | Santini et al. | |
| 7,794,490 B2 | 9/2010 | King | |
| 7,824,699 B2 | 11/2010 | Ralph et al. | |
| 7,892,221 B2 | 2/2011 | Santini, Jr. et al. | |
| 2005/0043738 A1 * | 2/2005 | Ryan | A61B 17/1604 606/80 |
| 2005/0283224 A1 * | 12/2005 | King | A61F 2/06 623/1.13 |
| 2007/0282425 A1 * | 12/2007 | Kleine | A61F 2/88 623/1.15 |
| 2008/0254095 A1 | 10/2008 | Ma et al. | |
| 2009/0029077 A1 | 1/2009 | Atanasoska et al. | |
| 2009/0311304 A1 * | 12/2009 | Borck | A61F 2/86 424/426 |
| 2010/0016957 A1 * | 1/2010 | Jager | A61K 9/0009 623/1.42 |
| 2010/0143437 A1 * | 6/2010 | Morris | A61K 9/0024 424/422 |
| 2010/0274280 A1 * | 10/2010 | Sawhney | A61B 17/00491 606/213 |
| 2014/0107423 A1 * | 4/2014 | Yaacobi | A61F 11/00 600/200 |

OTHER PUBLICATIONS

International Search Report for PCT/US2013/048614 dated Sep. 4, 2015.

* cited by examiner

*Primary Examiner* — Bhisma Mehta
*Assistant Examiner* — Jenna Zhang
(74) *Attorney, Agent, or Firm* — Rathe Lindenbaum LLP

(57) ABSTRACT

A therapeutic implantable device comprises a biodegradable outer shell, a plurality of spaced biodegradable layers within the outer shell, a first therapeutic mass between the plurality of spaced biodegradable layers and a second therapeutic mass between the plurality of spaced biodegradable layers. The plurality of spaced biodegradable layers are arranged such that the first therapeutic mass is exposed external to the implantable device before exposure of the second therapeutic mass external to the implantable device.

22 Claims, 6 Drawing Sheets

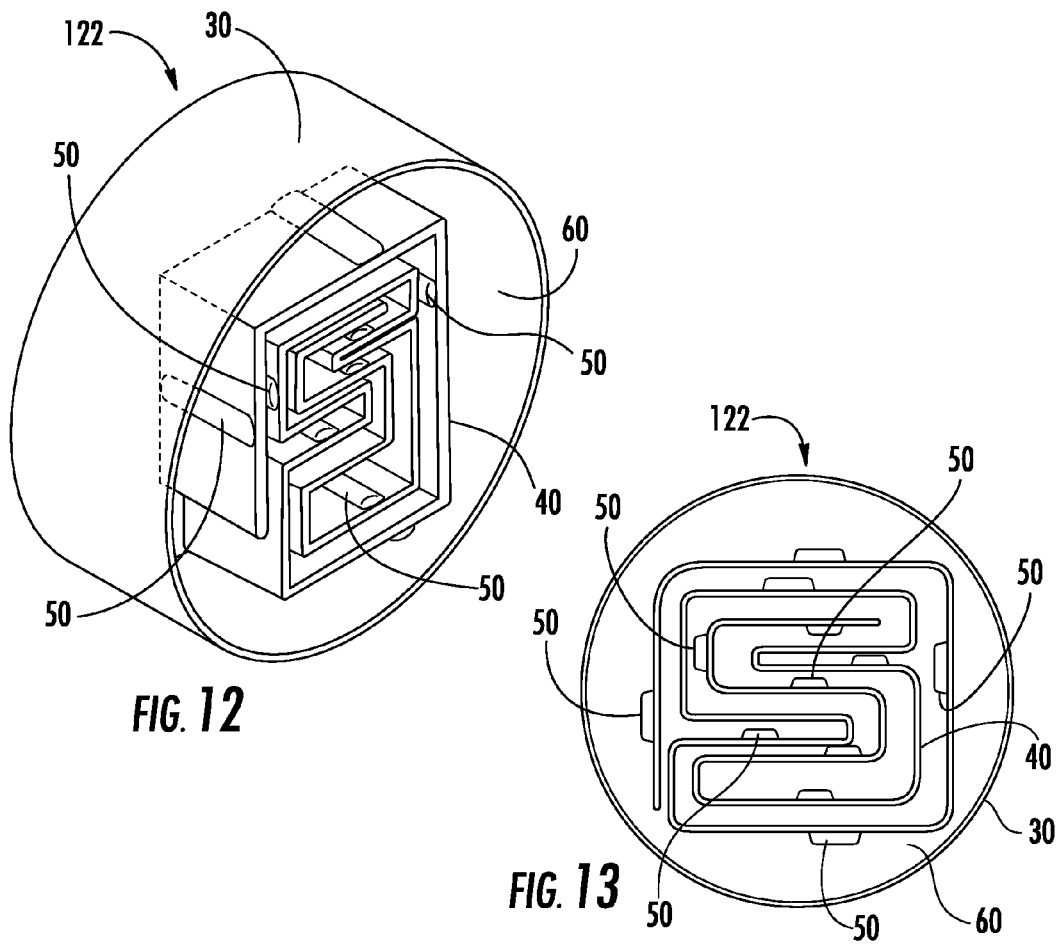
FIG. 12
FIG. 13
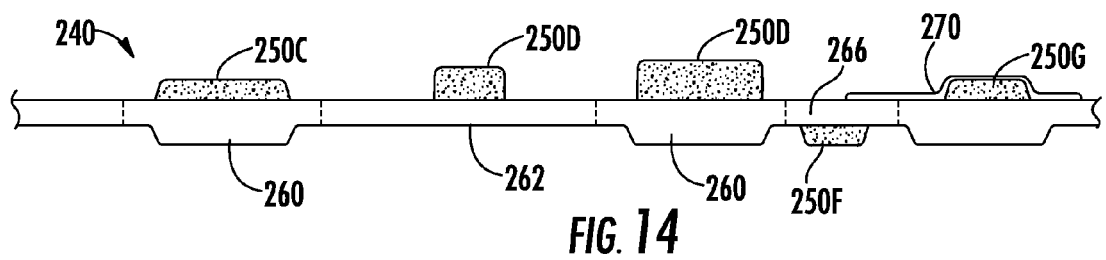
FIG. 14
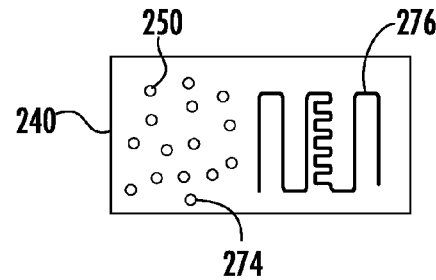
FIG. 14A

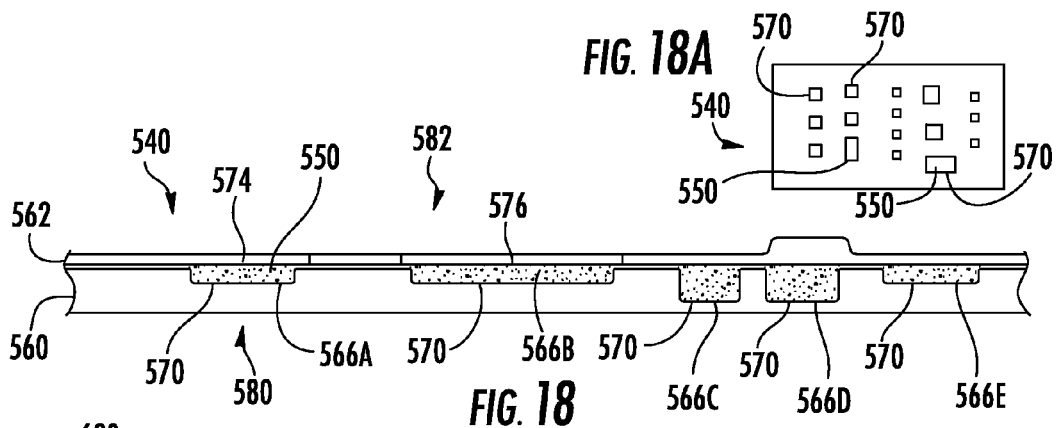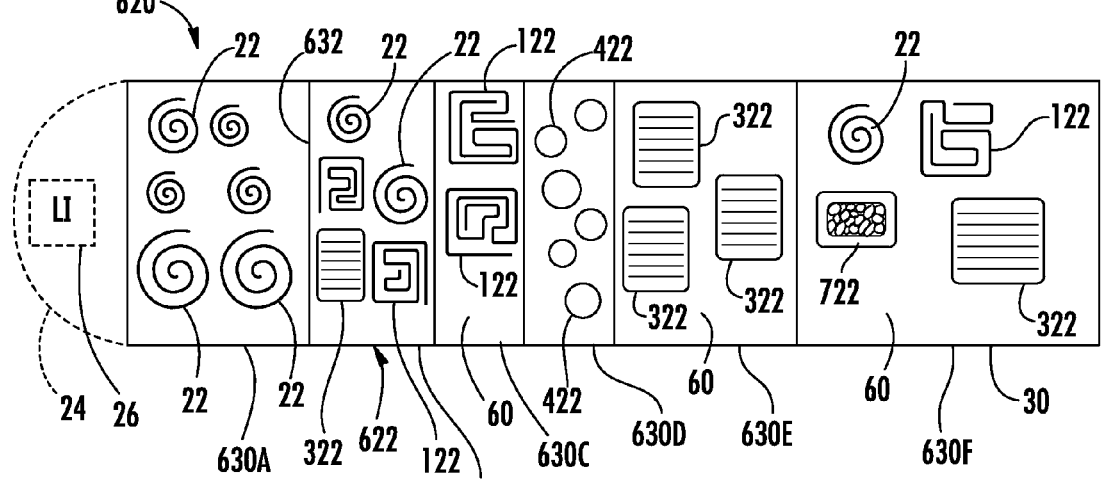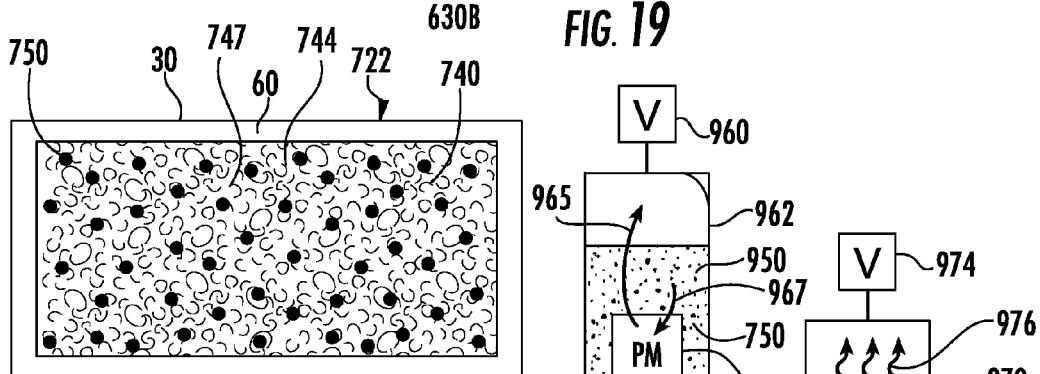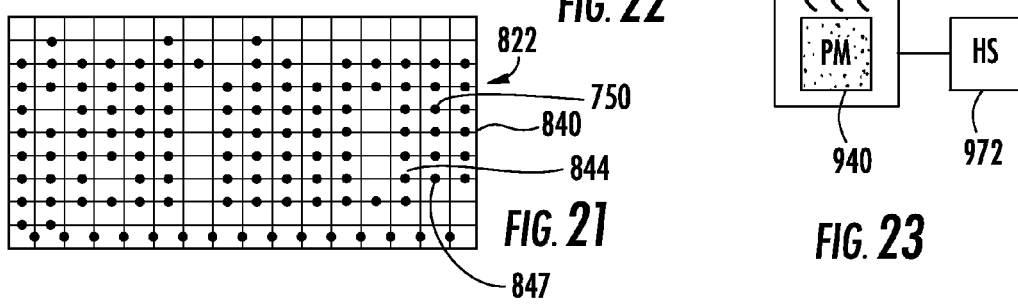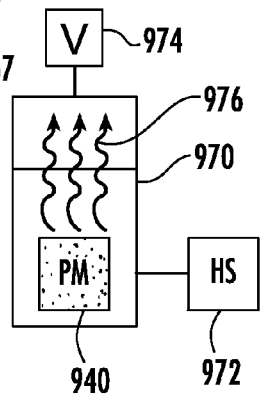

THERAPEUTIC IMPLANTABLE DEVICE

BACKGROUND

Therapeutics, vaccines, medicines and drugs (collectively referred to as therapeutics) are sometimes administered in liquid form via shots. In other circumstances, such therapeutics are delivered orally in the form of pills. In some circumstances, therapeutics are delivered via implants. Such therapeutic delivery systems are often complex and difficult to manufacture or are difficult to precisely control a timed release of different therapeutics.

BRIEF DESCRIPTION OF THE DRAWINGS

FIG. 12 is a perspective view of another example of the device of FIG. 1.

FIG. 13 is an end view of the device of FIG. 12.

FIG. 14 is a fragmentary sectional view of an example of a sheet and therapeutic) for forming an implant device.

FIG. 14A is a top plan view of an example of a sheet with an example pattern of therapeutics thereon prior to being folded.

FIG. 18 is a fragmentary sectional view of another example of a sheet and therapeutic for forming an implant device.

FIG. 18A is a top elevational view of an example sheet with an example pattern of therapeutics thereon for forming an implantable device.

FIG. 19 is a sectional view schematically illustrating another example of the therapeutic implant device of FIG. 1.

FIG. 20 is a sectional view illustrating another example of the therapeutic implant device FIG. 1.

FIG. 21 is a sectional view illustrating another example of the therapeutic implant device of FIG. 1.

FIGS. 22 and 23 are schematic diagrams illustrating an example method for forming the therapeutic implant device shown in FIG. 20 or FIG. 21.

DETAILED DESCRIPTION OF THE EXAMPLE EMBODIMENTS

Figure 1:
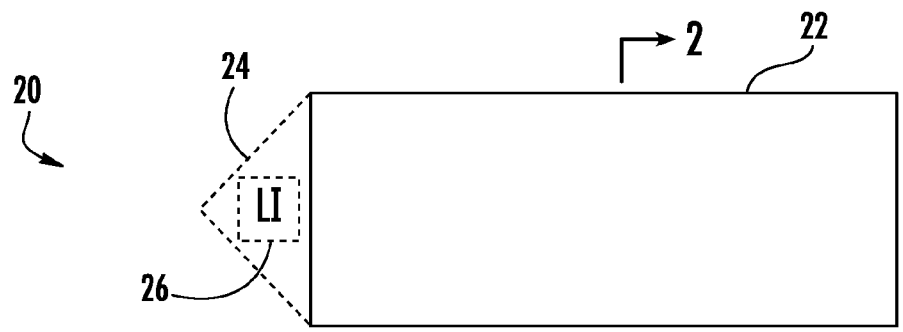
FIG. 1 is a side of an example therapeutic implant device.

FIG. 1 is a side elevational view illustrating an example therapeutic implantable device 20 configured to be implanted via a needle into a patient, such as a person or animal, for timed release of one or more therapeutics. As will be described hereafter, device 20 delivers or releases therapeutics in a precisely controlled time fashion using a less complex and more easily manufactured delivery structure. As shown by FIG. 1, device 20 comprises an elongated main body 22 containing such therapeutics. Although illustrated as an elongated cylinder, in other implementations, body 22 may comprise an elongated polygon, an elongated brick (prism), ellipsoid or a sphere. In other implementations, body 22 may have other 3D shapes. In one implementation, body 22 is configured to be implanted within a human anatomy, having a maximum length of 4 cm and a maximum width of 0.5 cm. In other implementations, body 22 may have other dimensions.

As shown in broken lines, in some implementations, device 20 may additionally include a pointed or rounded tip 24 to facilitate easier penetration into tissue with reduced damage to body tissue. In one implementation, tip 24 may include a location identifier 26 comprise a material facilitating identification of a location of implant device 20. For example, in one implementation, location identifier 26 may comprise a radioactive material, a radio opaque material or a sonogenic material, or assume a sonogenic shape, to allow real time precision placement, or post placement confirmation/identification In other implementations, location identifier 26 may comprise other sensing materials. In yet other implementations, tip 24 may be omitted.

Figure 2:
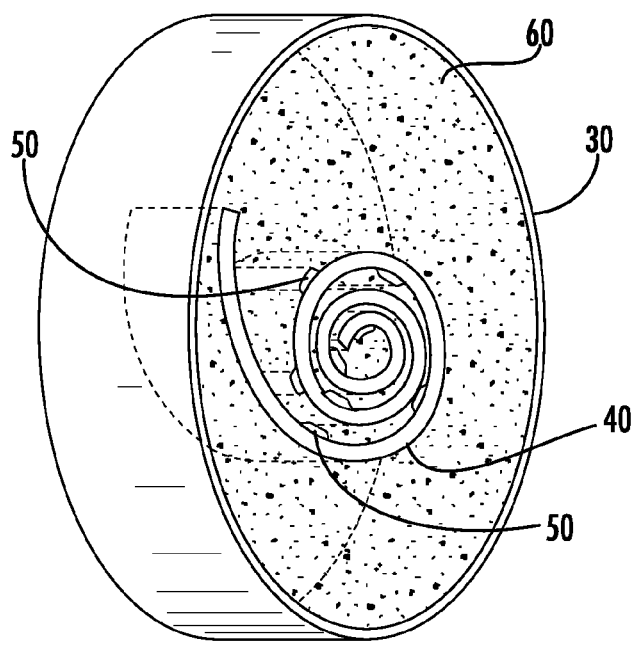
FIG. 2 is a fragmentary perspective view of an example of the device of FIG. 1.
Figure 3:
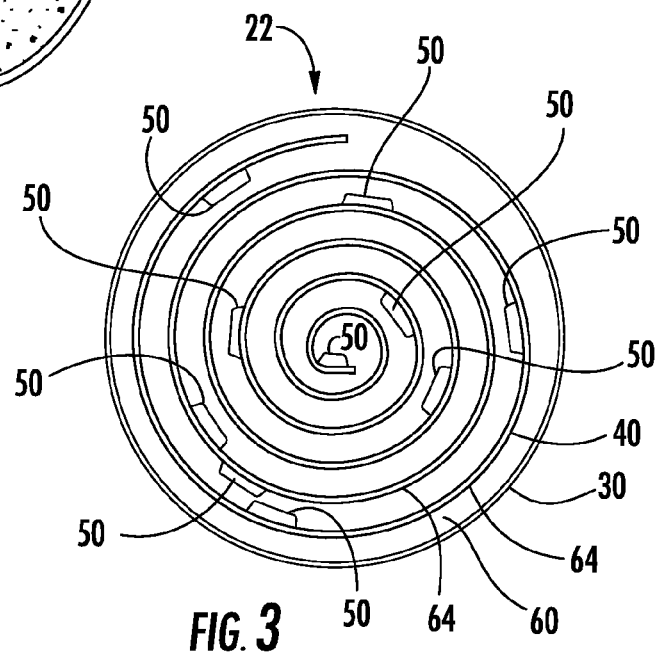
FIG. 3 is a sectional view of the device of FIG. 1 taken along line 2-2.

FIGS. 2 and 3 illustrate one example of body 22 of implant device 20. In the example illustrated in FIGS. 2 and 3, body 22 comprises outer shell 30, sheet 40 and therapeutic masses 50. Outer shell 30 comprises a wall of biodegradable material that encapsulates or surrounds sheet 40 and therapeutic masses 50. Examples of biodegradable materials from which outer shell 30 is formed or from which other biodegradable components of body 22 or device 20 are formed, such as sheet 40, include but are not limited to, a cellulose, or variants thereof, glycolic acid derived membranes or other materials forms, or their combinations, with characteristics such that the materials are biodegradable naturally and completely in the host body The degradation may be time controlled by two factors: the nature and amount of the material, and the final 3D configuration rendered via different wrapping, folding, spacing, differential chambering. Other industrial processing, such as ink jet like position, drying, vacuum, sponge absorption, may be utilized as well. The therapeutic will be pre-positioned in the 2D stage as different density and pattern, when wrapped or folded (or other method illustrated below) into a 3D configuration, such that its release profile will be tailored to its pharmacological goal: extended, time controlled, concentration range bound.

In one implementation, outer shell 30 contacts outermost surfaces of sheet 40. In other implementations, outer shell 30 may be formed by or may contain an inner core material 60 that extends between outer surfaces of shell 30 and sheet 40. In some implementations, the core material may fill spaces between the different layers formed by sheet 40. In one implementation, outer shell 30 is formed from a material or is coated with a material configured to inhibit or stop bleeding during its placement.

Sheet 40 comprises a single continuous panel of biodegradable material supporting or carrying therapeutic masses 50. In the example shown in FIG. 2, sheet 40 is wrapped such that the single panel of sheet 40 forms a plurality of spaced biodegradable layers 64 separating different therapeutic masses 50. For purposes of this disclosure, the term "wrapped" means that a single sheet is bent, wound or otherwise shaped such that portions of sheet 40 face one another or overlap one another. In the example illustrated, sheet 40 is illustrated as being helically or spirally wound. In other words, sheet 40 comprises a plane curve cross-section generated by point moving around a fixed point while constantly receding from or approaching the fixed point to form a helix. Although illustrated as being spirally wound as a cylinder having a circular cross-section, concentric about a centerline or axis, in other implementations, sheet 40 may be spirally wound by one or more axes so as to have an elliptical cross-section or multi-lobed cross-section. In other implementations, sheet 40 may be "wrapped" in other fashions.

Because sheet 40 is wrapped, outermost therapeutic masses 50 on sheet 40 may be exposed and therefore released at times before innermost therapeutic masses 50 on sheet 40. As a result, the time at which a therapeutic is exposed and thereby delivered or released into a body may be predefined or controlled based upon the relative inner or outer positioning of the therapeutic mass 50 on the various windings of sheet 40. For example, therapeutic mass 50G will be exposed and thereby released at a time much later than the release of therapeutic mass 50A.

Therapeutic masses 50 comprise medicinal materials supported or carried by sheet 40. Examples of therapeutic masses 50 include, but are not limited to, pharmaceuticals (chemotherapy agents, antibiotics, antiviral agents, anti-hypertension agents, vassodilatation agents, vasoconstriction agents, local anesthetics, NSAIDA, steroids, psychotropic agents, neurotropic agents), proteins (including antibodies, interferons and hormones, peptides (interleukins, RNA's) osteogenic and osteolytic agents, genetic altering agents and stem cells. Such therapeutics may be solid, semi-liquid or liquid.

In one implementation, each of therapeutic masses 50 may constitute the same therapeutic formulation in generally the same doses. In other implementations, some of therapeutic masses 50 may be different formulations or different doses of the same therapeutic formulation. For example, an outer therapeutic mass 50 may comprise a first type of therapeutic while and inner therapeutic mass 50 may comprise a different type of therapeutic. In one implementation, multiple therapeutic masses may be applied along sheet 40 in a desired sequence such that the different therapeutic masses are released in a sequenced manner. In the example illustrated in FIG. 2, therapeutic masses 50 are located on both sides of sheet 40. In other implementations, therapeutic masses 50 may be located on only one side of sheet 40.

Figure 4:
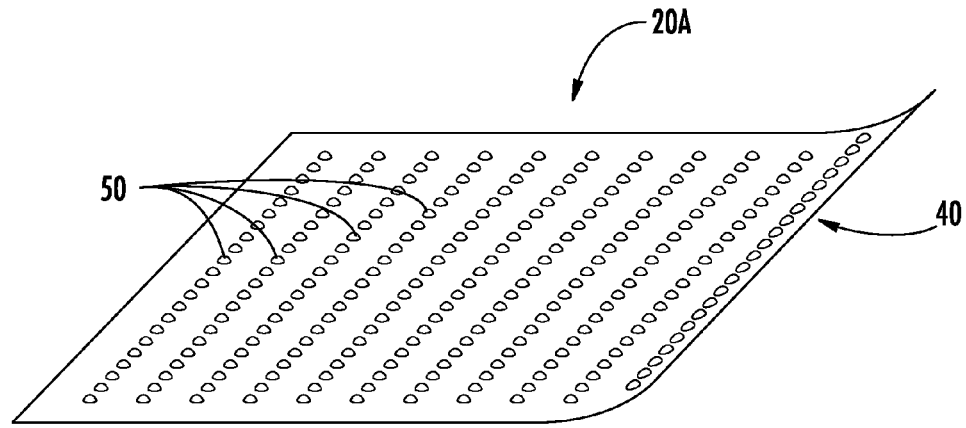
FIG. 4 is a perspective view of a biodegradable sheet having rows of therapeutics deposited thereon.
Figure 5:
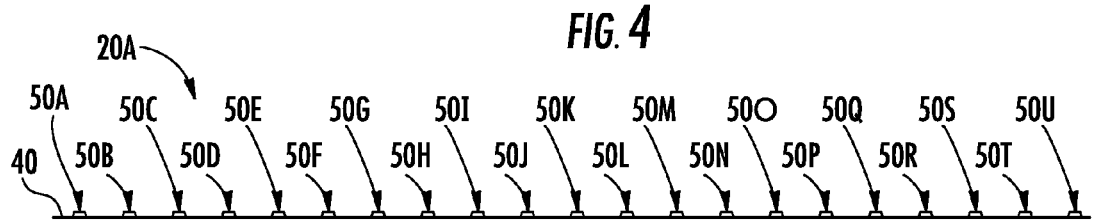
FIG. 5 is an end view of the biodegradable sheet with rows of therapeutics of FIG. 4.
Figure 6:
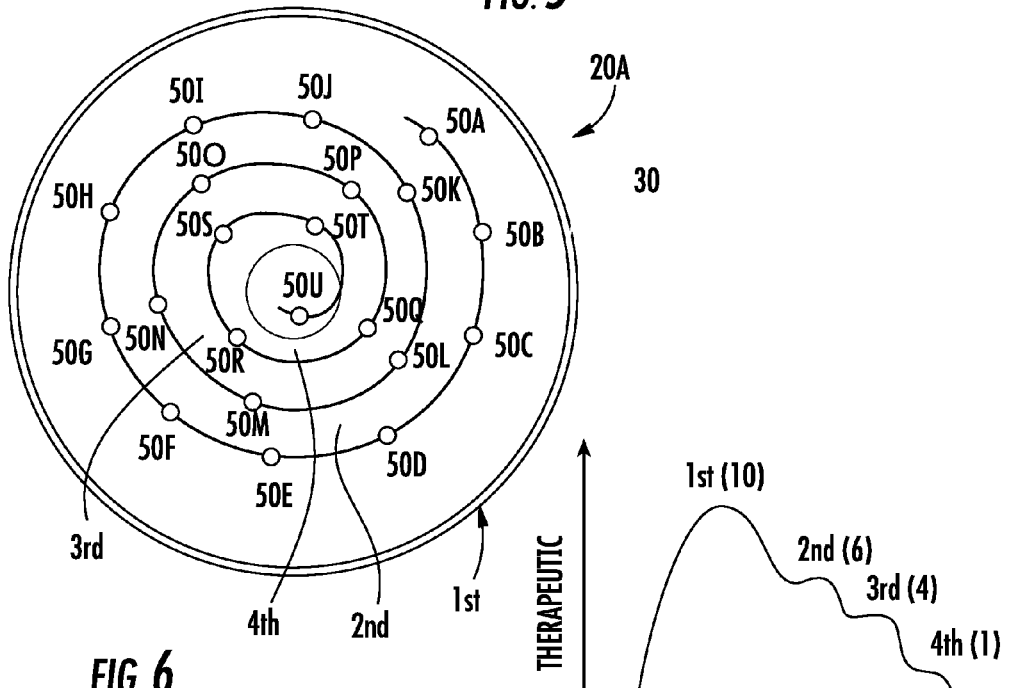
FIG. 6 is an end view of the biodegradable sheet of FIG. 5 spirally wound and enclosed within a shell to form an implantable device.
Figure 7:
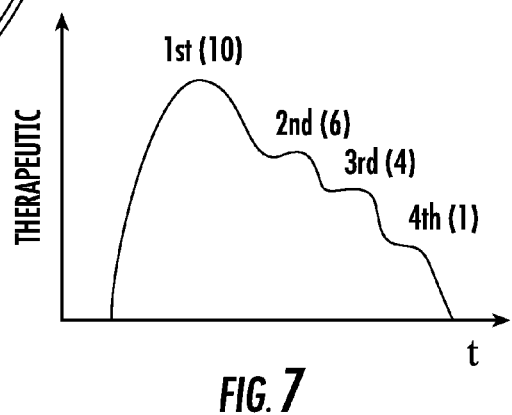
FIG. 7 is a graph illustrating the timed release of therapeutics from the implantable device of FIG. 6.

FIGS. 4-6 illustrate one example method of forming an implant device 20A, a particular example of implant device 20. Implant device 20A is identical to implant device 20 except that implant device 20A has the specific therapeutic release profile as shown in FIG. 7). As shown by FIGS. 4 and 5, while sheet 40 is substantially flat, therapeutic masses 50A-50U are deposited upon sheet 40. In the example illustrated, therapeutic masses 50A-50J each comprise a row of multiple spaced spots of therapeutics or continuous line of therapeutics, wherein the rows are evenly spaced across sheet 40. As shown by FIG. 6, after deposition or application of therapeutic masses 50A-50U, sheet 40 is wrapped (spirally wound in the illustrated example).

FIG. 7 is a graph illustrating the release of therapeutics over time with implant 20A. As shown by FIG. 6, the outermost winding has a largest circumference and therefore has the largest number of rows of therapeutics. The innermost winding has the smallest circumferential length, having the fewest number of rows of therapeutics. In the example illustrated, the outermost winding has 10 rows of therapeutics, the next inner winding has 6 rows of therapeutics, the next inward winding has 4 rows of therapeutics and the innermost winding or portion of sheet 40 has just 1 row of therapeutics. As implant 20A and the layers biodegradable material between the various windings breaks down, the therapeutics on the windings are sequentially exposed, sequentially releasing therapeutics, beginning with the outermost winding and finishing with the innermost winding. As shown by FIG. 7, implant 20A achieves a timed release of therapeutics wherein the largest amount of therapeutics is initially released and subsequent release of type UNIX are stepwise reduced over time.

Figure 8:
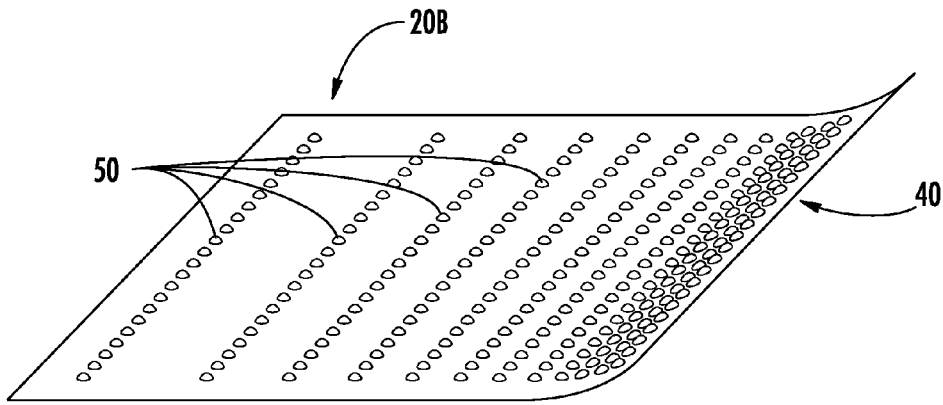
FIG. 8 is a perspective view of another biodegradable sheet having rows of therapeutics deposited thereon.
Figure 9:
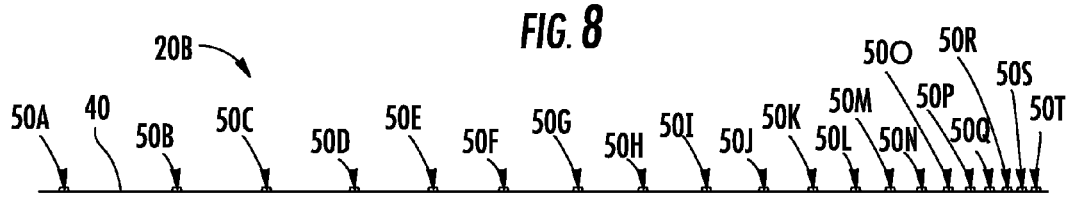
FIG. 9 is an end view of the biodegradable sheet with rows of therapeutics of FIG. 8.
Figure 10:
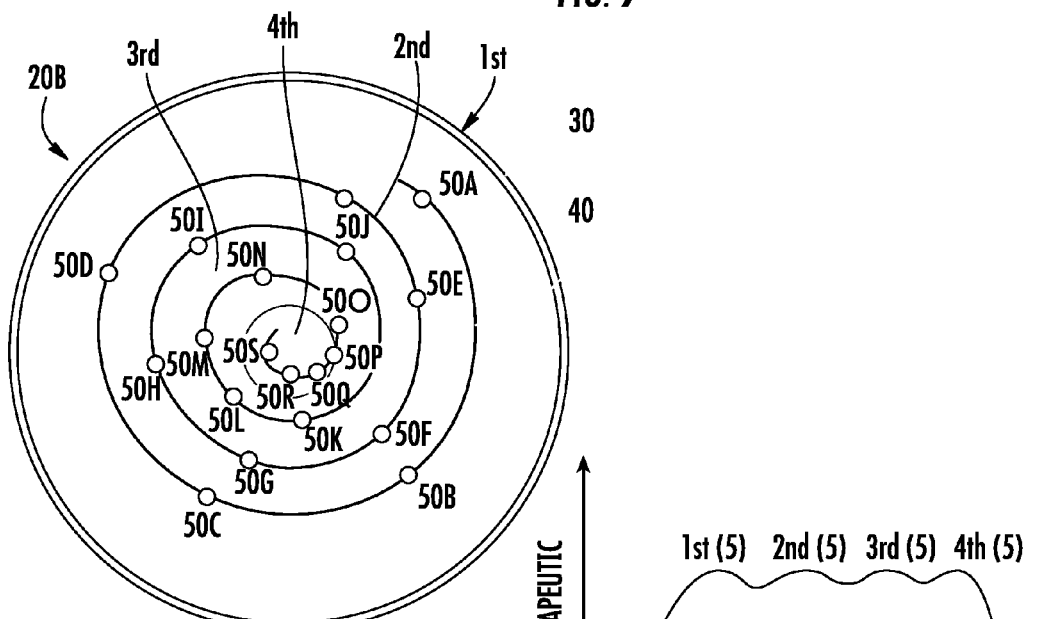
FIG. 10 is an end view of the biodegradable sheet of FIG. 5 spirally wound and enclosed within a shell to form an implantable device.
Figure 11:
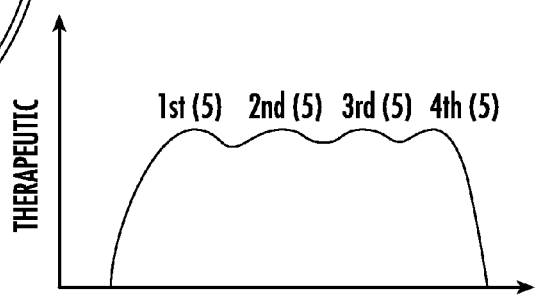
FIG. 11 is a graph illustrating the timed release of therapeutics from the implantable device of FIG. 10.

FIGS. 8-10 illustrate another example method of forming an implant device 20B, a particular example of implant device 20. Implant device 20B is identical to implant device 20 except that implant device 20B has the specific therapeutic release profile as shown in FIG. 11). As shown by FIGS. 8 and 9, while sheet 40 is substantially flat, therapeutic masses 50A-50T are deposited upon sheet 40. In one implementation, such therapeutic masses 50 are applied or deposited upon sheet 40 while sheet 40 is substantially flat, wherein after deposition of such therapeutic masses 50, sheet 40 is wrapped. In the example illustrated, therapeutic masses 50A-50T each comprise a row of multiple spaced spots of therapeutics or continuous line of therapeutics, wherein the rows are unevenly spaced across sheet 40. As shown by FIG. 10, after deposition or application of therapeutic masses 50A-50T, sheet 40 is wrapped (spirally wound in the illustrated example).

FIG. 11 is a graph illustrating the release of therapeutics over time with implant 20B. As shown by FIG. 9, therapeutic masses 50A-50T are non-uniformly deposited along sheet 40. In the example illustrated, therapeutic masses 50A-50T are non-uniformly or unevenly spaced such that each winding carries approximately the same number of rows of therapeutics. In the example illustrated, the outermost winding has a largest circumference and therefore has the largest spacing between rows of therapeutics. The innermost windings have smaller circumferences and smaller length, having the smallest spacing between rows of therapeutics. In the example illustrated, each of the windings or layers has five rows of therapeutics. In other implementations, the windings or layers may have a greater or fewer number of such rows. As implant 20B breaks down, the windings are sequentially exposed, sequentially releasing therapeutics, beginning with the outermost winding and finishing with the innermost winding. As shown by FIG. 11, implant 20B achieves a timed release of therapeutics wherein the amount of therapeutics is substantially constant over time (the fences same model therapeutics is released upon exposure of each of the layers or windings. As shown by implant 20A and implant 20B, the timing of therapeutic release as well as the amount of therapeutics provided at each therapeutic release may be varied and controlled by controlling the number of windings, the spacing of the windings and the spacing of the rows or other deposits of therapeutics along sheet 40 and amongst the layers.

In one implementation, therapeutic masses 50 may be printed upon sheet 40 such as with a drop-on-demand inkjet print head. As a result, the amount and location of each of therapeutic mass 50 may be precisely and accurately controlled. In other implementations, therapeutic masses 50 may be applied to one or both sides of sheet 40 using other techniques.

Once the therapeutic masses 50 have been applied to sheet 40, sheet 40 is wrapped. In other implementations, the therapeutic masses 50 upon sheet 40 may be sealed in place upon sheet 40 by applying one or more overcoats or films over sheet 40 to encapsulate the applied therapeutic masses 50. Such an overcoat or sealing layer may comprise a thin membrane of biodegradable material. After such sealing or lamination, layer 40 may be folded.

FIGS. 12 and 13 illustrate body 122, another example of body 22 of implant 20. Body 122 is similar to body 22 except that sheet 40 which therapeutic masses 50 is wrapped in a different manner. Instead of being spirally wound as sheet 40 as in body 22, sheet 40 is folded. In contrast to being spirally wound wherein sheet 40 is always extending inwardly or outwardly circumferentially about a centerline or axis, sheet 40 in body 122 is wrapped wherein sheet 40 extends in opposite directions at times. Although illustrated as being folded in the form of a square or rectangular cross-sectional shape, in other implementations, sheet 40 may be wrapped or folded with other folding patterns so as to have other cross-sectional shapes. This 3D configuration also started with a 2D membrane shown in FIG. 3A, with prepositioned 50. Then the membrane is folded multiple times as illustrated to its final 3D construction with the therapeutic release profile being changeable or controlled based on the different pattern of therapeutic masses 50 on the 2D membrane or sheet 40.

In each of the examples shown in FIGS. 2 and 12, the timed release of therapeutic masses 50 may be adjusted or controlled by adjusting factors such as how tight sheet 40 is wrapped or wound, the number of wraps or windings and the folding pattern (with respect to the example in FIG. 3). Identical sheets 40 having an identical patterns of deposit therapeutics may be provided with different time release characteristics by simply adjusting any of the aforementioned factors. In other implementations, the timed release of therapeutics (the timing at which therapeutics are released) may be adjusted further by adjusting the pattern at which therapeutic masses 50 are applied to sheet 40 prior to such wrapping.

FIG. 14 is a sectional view illustrating sheet 240 and therapeutic masses 250, an example implementation of sheet 40 and therapeutic masses 50, respectively, prior to wrapping. FIG. 4A is a top plan view of sheet 240 and therapeutic masses 250 prior to wrapping. Therapeutic masses 250 are the same as therapeutic masses 50 but for the varying of the density and patterning as will be described hereafter. As shown by FIG. 14, in addition to varying or controlling the release of therapeutics by varying wrapping characteristics of sheet 240, such release may also be adjusted are controlled by varying characteristics of sheet 240 itself or characteristics of the applied therapeutic masses 250.

As shown by FIG. 14, one technique for varying or controlling the release of therapeutic masses 250 is to vary a thickness of sheet 240 underlying therapeutic mass 250. In the example illustrated, sheet 240 is thicker in region 260 underlying therapeutic mass 250C then region 262 underlying therapeutic mass 250D. The thicker region 260 may result in therapeutic mass 250C being released are exposed at a later time as compared to an implementation where therapeutic mass 250C were deposited upon a region having a thickness of region 262.

As shown by FIG. 14, another technique for varying a controlling release of therapeutic masses 250 with device 22 is to vary the material or materials forming different portions of sheet 240. For example, region 262 underlying therapeutic mass 250D may form from a first biodegradable material which degrades at a much slower rate as compared to the biodegradable material forming region 266 supporting therapeutic mass 250F. As a result, even portions of layer 250 having the same thickness, may have different therapeutic release characteristics due to the different materials forming the different portions of sheet 240. In some implementations, both the material forming different regions of sheet 240 as well as the thicknesses of such different regions may be varied or controlled to vary the timing at which therapeutic masses 250 are delivered.

As shown by FIG. 14, another technique for varying or controlling release of therapeutic masses 250 with device 22 (or device 122) is to vary the exposed outer surface area of the therapeutic mass 250 on sheet 240. For example, a same amount of therapeutic mass 250 spread over a larger area sheet 240 may be more quickly exposed, released and absorbed (or dissolved) as compared to the same amount of therapeutic mass 250 deposited so as to be have a much smaller outer or exposed surface area.

FIG. 14 illustrates yet another example method by which release of therapeutic masses 250 may be adjusted. As shown by FIG. 14, once therapeutic masses 250 have been deposited upon sheet 240, such deposited therapeutics may be coated (such as with a laminate, a spray or the like) with an overlying biodegradable layer 270. The thickness of layer 270 may be varied to further adjust the timing of which a therapeutic (such as therapeutic mass 250G in the illustration) is released. Different coatings 270 may be formed from different materials as well to provide different release characteristics. In some implementations, coatings 270 may completely seal or encapsulate the particular therapeutic mass 250. In other implementations, coatings 270 may only partially cover the underlying therapeutic mass 250, wherein the coatings 2 study will still impact the rate at which the therapeutic mass 250 is released.

FIGS. 14 and 14A illustrate control over delivery of therapeutic masses 250 based upon deposition of therapeutic masses 250 upon sheet 240. As shown by FIG. 14, different regions of sheet 240 may have deposited thereon different volumes or amounts of therapeutics in different shapes or surface area extends. As shown by FIG. 14A, the release or delivery of therapeutic masses 250 may further be controlled across a length of body 22 (or body 122) by controlling the patterning of the therapeutic upon sheet 240. For example, therapeutic masses 250 may be applied to sheet 240 at spaced locations in the form of spots, patches, drops and the like (identified with reference numeral 274). Alternatively, therapeutic masses 250 may be applied sheet 240 in a continuous fashion along the surface of sheet 240. For example, therapeutic masses 250 may be applied, printed or deposited in a continuous line or series of line segments having different patterns depending upon the timing at which therapeutics are to be delivered. When the delivery of therapeutic mass 250 is to be more frequent or more intense, the particular therapeutic may be applied to an appropriate portion of sheet 240 at a high density of spots or a high density of line segments 276. Likewise, when the delivery of therapeutic masses 250 is to be more spaced out or less frequent, the spacing between such spots 254 or the density of line segments 276 on sheet 240 may be reduced. Use of drop-on-demand inkjet printing may facilitate accurate and precise control over deposition of therapeutic masses 250 upon sheet 240 with the desired spacings, densities or patterns. In some implementations, therapeutic masses 250 may be applied by being spread upon the surface of sheet 240.

Figure 15:
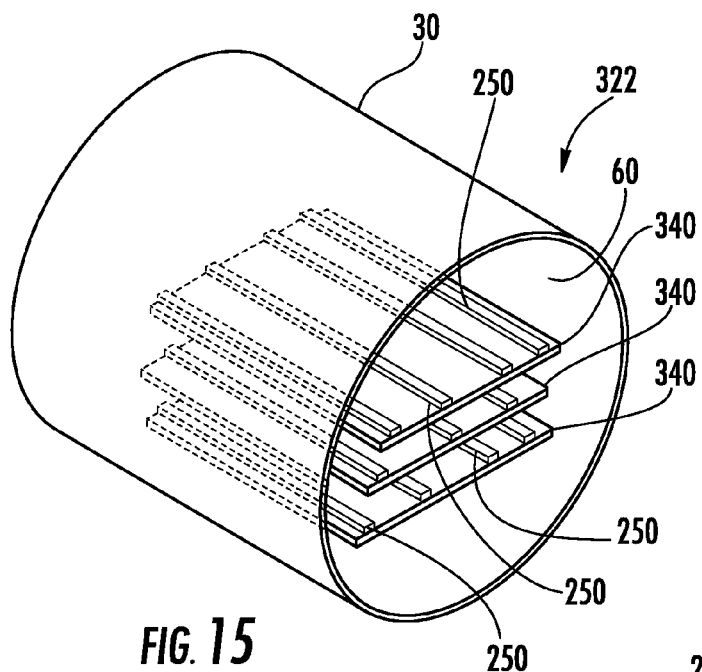
FIG. 15 is a fragmentary perspective view of another example of the device of FIG. 1.
Figure 16:
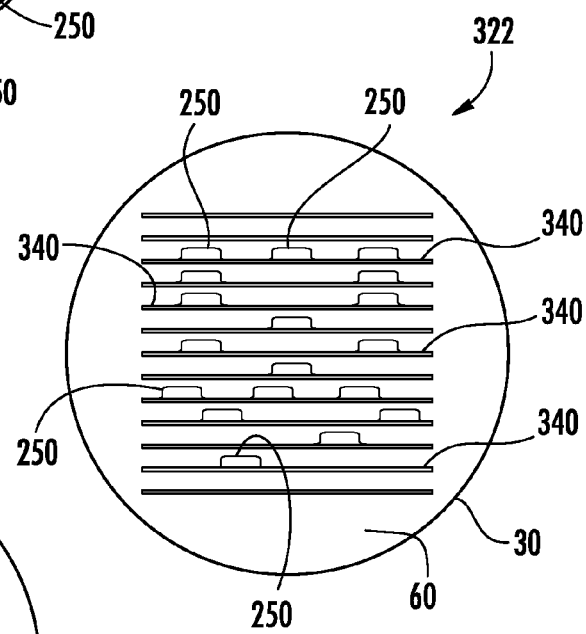
FIG. 16 is an end view of the device of FIG. 15.

FIGS. 15 and 16 illustrate body 322, another example implementation of body 22 of implant device 20. Body 322 is similar to body 22 except that instead of wrapping sheet 240 (or sheet 40), sheet 240 (or sheet 40) is severed or cut into a plurality of smaller sheets 340, some of which carry therapeutic masses 250. The multiple sheets 340 are then stacked such that the multiple sheets 340 form a plurality of spaced biodegradable layers between therapeutic masses 250. As shown in FIG. 5, some of layers 340 may omit therapeutic masses 250. As shown by FIG. 5, some layers 340 may include a single patch, spot or segment of a therapeutic mass 250 while other of layers 340 include multiple patches, spots or line segments of a same or different therapeutic mass 250. Although such sheets 340 may be formed by applying therapeutic mass 250 across a single continuous sheet 240 and then severing the sheet into smaller sheets 340, in other implementations, sheets 340 may be formed separately or may be cut from a larger sheet into smaller sheets 340, prior to the application of therapeutic masses 250.

Figure 17:
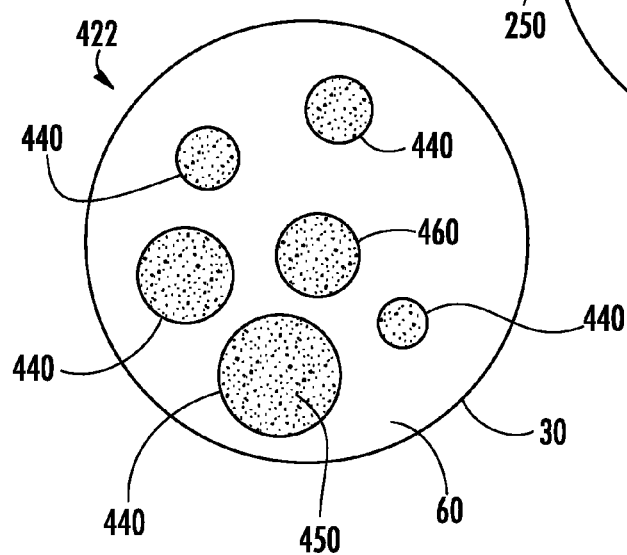
FIG. 17 is a sectional view of another example of the device of FIG. 1 taken along line 2-2.

FIG. 17 is a cross-sectional view illustrating body 422, another example implementation of body 22 of implant device 20. As shown by FIG. 17, body 422 comprises biodegradable outer shell 30 encapsulating our surrounding a plurality of spaced spheres 440, wherein each sphere 440 contains therapeutic particles 450 or therapeutics in other forms. In one implementation, spheres 440 are encapsulated are surrounded by core material 60 (described above). Each sphere 440 has opposite side walls which serve as biodegradable layers separating the therapeutic masses 450 within the different spheres 440. As shown by FIG. 17, the size and number of such spheres 440 and the amount or type of therapeutics contained within such spheres may be varied. For example, one sphere 440 may contain a first type of therapeutic while another sphere 440 contains a different type of therapeutic. In one implementation, different spheres 440 may have outer walls of different thicknesses or may have different inner core materials 460 encapsulating the inner therapeutic particles 450, wherein the different outer wall thicknesses are the different inner core materials for 60 provide different release times or release rates for the contained therapeutic masses 450.

FIG. 18 is a sectional view illustrating sheet 540 and therapeutic masses 550, an example implementation of sheet 40 and therapeutic masses 50, respectively, prior to wrapping. FIG. 18A is a top plan view of sheet 540 and therapeutic masses 550 illustrating the layout of therapeutic masses 550 across sheet 540 prior to wrapping. In the example shown in FIG. 18, sheet 540 comprises base panel 560 and cover panel 562.

Base panel 560 comprise a continuous sheet or panel of one or more biodegradable materials having cavities 566A, 566B, 566C, 566D and 566E (collectively referred to as cavities 566). Cavities 566 cooperate with cover panel 562 to form multiple compartments 574 encapsulating and containing therapeutic masses 550. In one implementation, cavities 566 are formed by removing material from a surface of panel 560. Such material removal may be performed by lasers, knives, chemical or physical etching, or by other material removal techniques. In yet other implementations, cavities 566 may be formed by selective addition of materials, such as through the use of masking, screening and the like. In other implementations, the pattern of cavities 566 in panel 560 may be formed through material shaping or deformation. For example, in some implementations, cavities 566 may be formed by embossing panel 560 while panel 560 is in an at least partially malleable or moldable state. In yet other implementations, cavities 566 may be formed by corrugating, bending or folding panel 560, wherein undulations in panel 560 form such cavities 566.

Cover panel 562 comprises a panel or sheet of one or more biodegradable materials joined to panel 560 to form chambers 570 so as to encapsulate or contain therapeutics within chambers 570. In one implementation, cover panel 562 is laminated to base panel 560 through welding, biodegradable adhesives and the like. Those portions of cover panel 562 overlying or extending across cavities 566 form caps for such cavities 566 to form chambers 570. Although each of the cavities 566 are illustrated as being closed or capped off with a single continuous cover panel 562, in other implementations, individual cavities 566 or subsets of such cavities 566 may be closed or capped off by separate individual cover panel 562.

Therapeutic masses 550 may comprise a same or different therapeutics of any of the type described above with respect to therapeutic masses 50. In one implementation, therapeutic masses 550 are applied to or deposited within their associated cavities 566 prior to joining of the one or more cover panels 562 to base panel 560. Such deposition of therapeutics may be carried out with a drop-on-demand inkjet printer, dispensing needles and the like. In other implementations, therapeutic masses 550 may be injected into cavities 566 of compartments 570 after such compartments 570 have been otherwise closed or sealed off by the one or more cover panels 562. For example, in some implementations, base panel 560 or cover panel 562 may be formed from a biodegradable material that function similar to a septum, allowing insertion of a needle or probe there through to allow therapeutics to be injected into a compartment 570, whereupon withdrawal of the needle or probe, the biodegradable material re-closes and re-seals.

FIGS. 18 and 18A illustrate various architectures and layouts by which the delivery of therapeutic masses 550 may be controlled using sheet 540 and therapeutic masses 550. As shown by FIG. 18A, the size and location of compartments 570 may be varied across sheet 540 to vary the amount of the therapeutic that is delivered as well as the timing at which such therapeutic is released (depending upon where the particular chamber 570 is formed on sheet 540 and how the sheet 540 is wrapped (wound or folded).

As shown by FIG. 18, the rate at which a therapeutic is released may be varied by adjusting or controlling the shape of the particular cavity 566. For example, an amount of therapeutics spread across a larger surface area of a shower, but wider and/or longer cavity 566 may be released or delivered at a faster rate as compared to the same amount of therapeutics contained in a deeper, but narrower (smaller opening) cavity 566. As noted above, in some implementations, a particular therapeutic mass 550, itself, may comprise therapeutic particles encapsulated within a biodegradable matrix that must dissolve for the therapeutic particles to be released and delivered.

As further shown by FIG. 18, the rate at which therapeutics are released or the timing at which such therapeutics are released may also be controlled by either varying the materials forming different caps of different compartments 570 or by varying the thickness of such different caps of different departments 570. For example, in one implementation, region 574 above cavity 566A may be formed from a biodegradable material that dissolves or otherwise degrades at a rate different than the biodegradable material or materials forming region 576 above cavity 566B. In one implementation, the thickness of cover panel 562 above cavity 566C (the cap of cavity 566C) is thinner as compared to the thickness of cover panel 562 above cavity 566D (the cap of cavity 566d). As a result, if such caps are otherwise the same and form from the same filler materials, the cap of cavity 566C may completely degrade before the cap of cavity 566D, releasing or delivering those therapeutics within cavity 566C before those therapeutics in cavity 566D.

In some implementations, the release of therapeutics may be controlled or varied amongst different compartments 570 by varying and controlling the depth of such compartments 570 with respect to the side of base panel 560 opposite to cover panel 562. For example, a cavity 566 may be sufficiently deep such that base panel 560 adjacent to a compartment 570 may degrade before or at the same time as the completion of degradation of the cap overlying the same compartment 570, allowing therapeutic masses 550 to be released from both sides of sheet 540. In the example illustrated in FIG. 18, cavity 566C is deeper than cavity 566B such that a bottom of compartment 574 from cavity 566C may become exposed (broken into) to release therapeutics from side to 580 of sheet 540 prior to such an occurrence, if at all, through panel 560 opposite to cavity 566B. In some implementations, some cavities 566 may be configured to release therapeutics from both sides of sheet 540 while other of cavities 566 deliver therapeutics only through one side, either side 580 or side 582 of sheet 540.

In addition to controlling or varying the thickness of base panel 560 adjacent to cavities 556 to control the timing and rate at which therapeutic masses 550 are delivered, such delivery of therapeutic masses 550 may also be controlled by varying the biodegradable materials that form those regions or portions of base panel 560 adjacent to the different compartments 570. For example, portions of base panel 560 adjacent to cavity 566A may be selected chosen so as to biodegrade at a faster rate as compared to the bottom ratable material or materials forming those portions or regions of base panel 560 adjacent to cavity 566B. In some implementations, the materials chosen for base panel 560 (or cover panel 562) may be chosen to biodegrade at different rates due to the different therapeutic masses 550 or matrix material of such therapeutics contained within a cavity 566. For example, even though the material or materials of panel 560 and panel 562 may be the same adjacent to cavities 566A and 566B, such cavities 566A and 566B may contain different therapeutics are different therapeutic solvents or matrices that react differently with the material or materials forming panel 560 are forming panel 562. As a result, the particular material or material chosen for either of panel 560 or panel 562 in conjunction with the different characteristics of the therapeutic mass 550 or its surrounding matrix a result in a different time release of the different therapeutics.

Sheet 540 may be utilized to form body 22 of implant device 20. As described above, sheet 540 may be wrapped, such as being spirally wound as in FIG. 2 or folded as in FIG. 3 prior to being surrounded by outer shell 30. Sheet 540 may alternatively be severed or cut into individual smaller sheets and then stacked as in FIG. 15. In some implementations, multiple sheets 540 may be formed separately (not cut from a single sheet) and then stacked prior to being surrounded by outer shell 30.

In some implementations, sheet 540 (with therapeutic masses 550) may be implanted as a sheet (without being wound, folded or otherwise wrapped). In some implementations, outer shell 30 or core material 60 may be omitted. For example, in each of the examples shown in FIGS. 2, 12 and 15, outer shell 30 and core material 60 may be omitted. In such implementations, body 22 may merely comprise the wrapped (wound or folded) or stacked arrangement of one or more sheets 40, 240, 340 or 540.

FIG. 19 schematically illustrates implantable device 620, another implementation of implantable device 20. Implantable device 620 similar to implantable device 20 except that implantable device 620 has a body 622 comprising multiple chambers 630A, 630B, 630C, 630D, 630E and 630F (collectively referred to as chambers 630). In addition to having an outer shell 30 and core material 60, body 622 includes intermediate biodegradable walls 632 that separate and form such chambers 630. Each of such chambers contains different therapeutics or different combinations of therapeutics in one implementation, each of such chambers 630 may have a different biodegradable core material 60 or a different biodegradable material or materials forming the adjacent outer shell portion 32 barrier control the rate of therapeutic delivery amongst the chambers. In the example illustrated, each of chambers 630 includes a different type of therapeutic delivery system including multiple smaller or miniature therapeutic delivery systems.

In the example illustrated, chamber 630A encloses or contains therapeutic delivery system similar to those shown in FIG. 2 form from sheet 240 or sheet 540. Chamber 630B encloses or contains multiple different therapeutic delivery systems similar to those shown in FIGS. 2, 12 and 15 formed from sheet 240 or sheet 540. Chamber 630C contains a single type of therapeutic delivery system similar to those shown in FIG. 12 and formed from sheet 240 or sheet 540. Chamber 630D encloses therapeutic delivery systems similar to those described with respect to FIG. 6. Chamber 630E contains are encloses therapeutic delivery systems similar those found in FIG. 15 and formed from sheet 240 or sheet 540. Chamber 630F surrounds or contains therapeutic delivery systems similar to those found in FIGS. 2, 12 and 15 and formed from sheet 240 or sheet 540.

Because chambers 630 include different types of therapeutic delivery systems, the rate at which therapeutics are delivered from such different chambers may be varied and controlled. For example, one delivery system may deliver therapeutics at a different rate or with different sequencing as compared to another delivery system. The combinations of delivery systems may be customized to provide a precisely controlled timing for the delivery of one or more therapeutics. In some implementations, different chambers 630 may contain different therapeutics are differ materials serving different functions. For example, in one implementation, one of chambers may contain material to facilitate tracking of a location of implant device 620. Examples of such materials may include the radio opaque material or a sonogenic material. At the same time, another of the chambers may contain a therapeutic while a third chamber contains a prophylactic antibiotic to decrease risk of infection post-implementation of the implant device inside the human or animal body. Although such chambers are illustrated as being in series along a length of device 620, in other implementations, such chambers may be formed within other chambers, make stand side-by-side in a radial or circumferential layout, or may have other arrangements.

FIG. 20 is a sectional view of body 722, another example of body 22 of therapeutic implant device 20. Body 722 is similar to each of bodies 22, 122, 322 and 422 in that it facilitates a controlled time delayed release of therapeutics into a person or animal. Body 722 comprises shell 30 and core material 60 (described above) and porous member 740. Porous member 740 comprises a three-dimensional mass of the biodegradable material having open cells or open pores 744. Such cells or pores 744 are open and that they are interconnected to one another, allowing liquid to be absorbed by force member 740 such that inner cells or pores 744 may receive and contain liquid pass along through the series of cells or pores 744 are connected to the inner selves or pores 744 and extending to the outer perimeter of member 740. The walls 747 of such cells or pores 744 support, carry or are coated with therapeutic masses 750. Walls 747 form a plurality of layers throughout member 740 with such layers extending between portions of therapeutic masses 750.

Therapeutic mass 750 is similar to therapeutic masses 50, 250, 450 and 550 described above. Therapeutic mass 750 can be used en bloc as an implant, or wrapped, folded, stacked, etc. As before in FIGS. 2, 12, 15, or used as building block as 50 etc. When the implant 20 having body 722 is placed within an animal or human patient, outer shell 50 and core material 60 degrade. Thereafter, body 740 may begin to degrade and breakdown. As body 740 breaks down in degrades, therapeutic masses 750 are exposed and released. Innermost therapeutic masses 750 are released at later times since such innermost therapeutics are not exposed until outer layers of body 740 (walls 744) have broken down or biodegraded.

To adjust the timing of which therapeutic masses 750 are subsequently released, the density of the cells or pores may be adjusted. A greater density of cells or pores may result in a slower release of therapeutic masses 750 as more intervening layers must degrade or breakdown to expose inner therapeutic masses 750. A single body 740 may include different regions of different densities to achieve different non-uniform release rates. In some implementations, the intensity or concentration of therapeutic masses 750 (within liquid 950 described below) deposited or loaded into such cells or along such cells may be increased or decreased depending upon the corresponding density of pores or cells to achieve a desired rate of therapeutic release.

In the example illustrated, body 740 comprises a foam or sponge open celled material. In the example illustrated, body 740 comprises a biodegradable polymeric material in the form of a foam or sponge. In other implementations, body 740 may be formed from other biodegradable materials or may have other configurations to facilitate the absorption and retention of the liquid. In other implementations, shell 30 and/or core material 60 may be omitted.

FIG. 21 is a sectional view of body 822, another example of body 22 of therapeutic implant device 20. Body 822 is similar to each of bodies 22, 122, 322, 422 and 722 in that it facilitates a controlled time delayed release of therapeutics into a person or animal. Body 822 comprises porous member 840. Although illustrated as omitting shell 30 and core material 60, in other implementations, body 822 may additionally include shell 30 and/or core material 60. Porous member 840 comprises a three-dimensional mass of the biodegradable material having open cells or open pores 844. Such cells or pores 844 are open and are interconnected to one another, allowing liquid to be absorbed by member 840 such that inner cells or pores 844 may receive and contain liquid passed along and through the series of cells or pores 844 that are connected to the inner cells or pores 844 and which extend to the outer perimeter of member 840. The walls 847 of such cells or pores 844 support, carry or are coated with therapeutic masses 750. Walls 847 form a plurality of layers throughout member 740 with such layers extending between portions of therapeutic masses 750. Body 822 can be used in the form of a block as an implant, or may be wrapped, folded or stacked as before in FIGS. 2, 12 and 15.

Therapeutic masses 750 are similar to therapeutic mass 50, 250, 450 and 550 described above. When the implant 20 having body 822 is placed within an animal or human patient, body 840 begin to degrade in breakdown. As body 840 breaks down and degrades, therapeutic masses 750 are exposed and released. Innermost therapeutic masses 750 are released at later times since such innermost therapeutics are not exposed until outer layers of porous member 840 (walls 844) have broken down or biodegraded. In the example illustrated, body 840 comprises a three-dimensional reticulated structure, such as a three-dimensional textile, matrix or grid of biodegradable material having interconnected cells or pores into which liquid may be wicked.

In one implementation, porous member 840 may be woven. In another implementation, porous member 840 may be formed by sintering or by pressing a powder in a die. In yet other implementations, porous member 840 may be formed in other fashions.

FIGS. 22 and 23 schematically illustrate one example method of loading a porous member 940 (which may constitute a porous member such as porous member 740 or porous member 840) with therapeutic masses 750. As shown by FIG. 22, porous member 940 is dipped or submersed in a volume of liquid 950 containing either dissolved or suspended therapeutic particles 750. During such submersion, a vacuum from vacuum source 960 is applied to the container 962 containing liquid 950. The applied vacuum causes trapping gas or air within porous member 943 sucker drawn out of porous member 940 as indicated by arrow 965. As indicated by arrow 967, liquid 950 and therapeutic particles 750 are drawn into porous member 940 replacing the evacuated gas. The vacuum applied by source 960 creates a force so as to draw liquid 950 and particles 750 into porous member 940.

As illustrated in FIG. 23, the saturated or soaked porous member 940 is subsequently placed in a heating chamber 970 in which heat is applied to porous member 940 by heat source 972 to dehydrate porous member 940, evaporating the liquid (water or solvent) absorbed into porous member 940. In the example illustrated, vacuum source 974 additionally applies a vacuum to the interior of the heating chamber 970. As a result, the heat required to dehydrate porous member 940 is less, wherein the lower temperatures may result in less damage to therapeutic masses 750 or porous member 940. In other implementations, vacuum 974 may be omitted. As indicated by arrows 976, the liquid 950 saturating porous member 940 is removed from porous member 940, leaving the therapeutic particles 750 within and throughout porous member 940, coded upon the walls of such cells or pores. In embodiments where the implant has a core material 60 are shell 30, such additional structures may be subsequently added to porous the member 940. In other implementations, porous member 940 may be loaded with therapeutic masses 750 in other fashions. Again, the product of this process can be used individually as a core material, or rolled, folded, wrapped as before.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible.

For example, unless specifically otherwise noted, the claims reciting a single particular element also encompass a plurality of such particular elements.

What is claimed is:

1. A therapeutic implantable device comprising:
a biodegradable outer shell;
a plurality of spaced biodegradable layers within the outer shell, the plurality of spaced biodegradable layers comprising innermost layers defining a space between the innermost layers;
a first therapeutic mass between the plurality of spaced biodegradable layers;
a second therapeutic mass between the plurality of spaced biodegradable layers, wherein the plurality of spaced biodegradable layers are arranged such that the first therapeutic mass is exposed external to the implantable device before exposure of the second therapeutic mass external to the implantable device; and
a biodegradable fill material filling the space defined between the innermost layers.

2. The therapeutic implantable device of claim 1 comprising:
a first completely enclosing compartment formed by the plurality of spaced biodegradable layers and enclosing the first therapeutic mass; and
a second completely enclosing compartment formed by the plurality of spaced biodegradable layers and enclosing the second therapeutic mass.

3. The therapeutic implantable device of claim 2, wherein the plurality of spaced biodegradable layers comprises a first layer having a first cavity in which the first therapeutic mass is disposed and a second layer forming a first cap over the first cavity.

4. The therapeutic implantable device of claim 3, wherein the plurality of spaced biodegradable layers comprises the first layer having a second cavity in which the second therapeutic mass is disposed and a third layer forming a second cap over the second cavity.

5. The therapeutic implantable device of claim 4, wherein the first cap has a first thickness and wherein the second cap has a different thickness.

6. The therapeutic implantable device of claim 4, wherein the first cap is configured to biodegrade at a first rate in a living body while the second cap degrades at a second rate different than the first rate in the living body.

7. The therapeutic implantable device of claim 2, wherein the first completely enclosing compartment and the second completely enclosing compartment are stacked upon one another within the outer shell.

8. The therapeutic implantable device of claim 2, wherein the first completely enclosing compartment and the second completely enclosing compartment are formed as part of a sheet that is spirally wrapped within the outer shell.

9. The therapeutic implantable device of claim 1, wherein the plurality of spaced biodegradable layers are formed by a single wrapped sheet.

10. The therapeutic implantable device of claim 9, wherein the single sheet is spirally wound.

11. The therapeutic implantable device of claim 9, wherein the single sheet is folded.

12. The therapeutic implantable device of claim 9, wherein the first therapeutic mass is coated upon a first portion and has a first thickness and wherein the second therapeutic is coated upon a second portions and has a second thickness different than the first thickness.

13. The therapeutic implantable device of claim 1 comprising:
a first wrapped sheet comprising the plurality of spaced biodegradable layers, the first therapeutic mass and the second therapeutic mass, wherein the first therapeutic mass and the second therapeutic mass are located on different portions of the first wrapped sheet such that the first therapeutic mass is exposed external to the implantable device before exposure of the second therapeutic mass external to the implantable device; and
a second wrapped sheet within the outer shell, the second wrapped sheet comprising:
a second plurality of spaced biodegradable layers within the outer shell;
a third therapeutic mass between the second plurality of spaced biodegradable layers; and
a fourth therapeutic mass between the second plurality of spaced biodegradable layers, wherein the third therapeutic mass and the fourth therapeutic mass are located on different portions of the second wrapped sheet such that the third therapeutic mass is exposed external to the implantable device before exposure of the fourth therapeutic mass external to the implantable device.

14. The therapeutic implantable device of claim 13, wherein the first wrapped sheet and the second wrapped sheet are either folded or spirally wound.

15. The therapeutic implantable device of claim 1, wherein the first therapeutic mass comprises a first therapeutic formulation and wherein the second therapeutic mass comprises a second therapeutic formulation different than the first therapeutic formulation.

16. The therapeutic implantable device of claim 1, wherein the plurality of spaced biodegradable layers are formed by a plurality of stacked sheets within the outer shell.

17. The therapeutic implantable device of claim 16, wherein the first therapeutic mass is coated upon a first sheet of the plurality of stacked sheets and wherein the second therapeutic mass is coated upon a second sheet of the plurality of stacked sheets.

18. The therapeutic implantable device of claim 17, wherein the first sheet has a first thickness and wherein the second sheet has a second thickness different than the first thickness.

19. The therapeutic implantable device of claim 1, wherein the first therapeutic mass and the second therapeutic mass each have a same therapeutic formulation.

20. The therapeutic implantable device of claim 1, wherein the plurality of spaced biodegradable layers comprises a porous member having pores between the layers and wherein the first therapeutic mass and the second therapeutic mass reside on the layers adjacent to different pores.

21. The therapeutic implantable device of claim 1, wherein the first therapeutic mass and the second therapeutic mass comprise particles and wherein the plurality of spaced biodegradable layers comprise biodegradable coatings on the particles.

22. The therapeutic implantable device of claim 1, further comprising a sensing agent between the plurality of spaced biodegradable layers.

* * * * *